(12) United States Patent
Herman

(10) Patent No.: US 10,813,438 B1
(45) Date of Patent: Oct. 27, 2020

(54) BARCODE SCANNER GLOVE WITH THUMB ACTIVATION

(71) Applicant: Valerie Herman, Mesa, AZ (US)

(72) Inventor: Valerie Herman, Mesa, AZ (US)

( * ) Notice: Subject to any disclaimer, the term of this patent is extended or adjusted under 35 U.S.C. 154(b) by 0 days.

(21) Appl. No.: 16/714,765

(22) Filed: Dec. 15, 2019

(51) Int. Cl.
*A45F 5/00* (2006.01)
*A61F 5/01* (2006.01)
*A47F 13/08* (2006.01)

(52) U.S. Cl.
CPC .............. *A45F 5/00* (2013.01); *A47F 13/08* (2013.01); *A61F 5/0118* (2013.01); *A45F 2005/002* (2013.01); *A45F 2005/008* (2013.01); *A45F 2200/05* (2013.01)

(58) Field of Classification Search
CPC .......... A45F 2005/008; A45F 2005/002; A45F 5/00; A45F 2200/0516; A45F 2200/05; A47F 13/08; A61F 5/0118; G06F 1/163; G06F 3/014
See application file for complete search history.

(56) References Cited

U.S. PATENT DOCUMENTS

| 5,340,972 | A | | 8/1994 | Sandor | |
|---|---|---|---|---|---|
| 5,514,861 | A | * | 5/1996 | Swartz | G06F 1/163 235/462.44 |
| 5,587,577 | A | * | 12/1996 | Schultz | G06K 7/10881 235/462.44 |
| 5,675,138 | A | | 10/1997 | La | |
| 5,808,289 | A | | 9/1998 | Becker | |
| 6,234,393 | B1 | | 5/2001 | Paratore et al. | |
| 6,688,526 | B2 | | 2/2004 | Metlitsky et al. | |
| 8,196,787 | B2 | * | 6/2012 | Strandberg | A45F 3/14 224/217 |
| 8,371,506 | B2 | | 2/2013 | Lee | |
| 9,224,027 | B2 | | 12/2015 | Van Horn et al. | |
| 2009/0272811 | A1 | | 11/2009 | An | |
| 2011/0224498 | A1 | * | 9/2011 | Banet | A61B 5/6824 600/300 |
| 2014/0249944 | A1 | * | 9/2014 | Hicks | G06Q 30/0281 705/17 |

OTHER PUBLICATIONS

Koamtac Finger Trigger Glove accessed on Sep. 5, 2019 from https://store.koamtac.com/products/finger-trigger-glove-for-kdc200.
Rufus Scanglove accessed on Sep. 5, 2019 from https://www.getrufus.com/wearablesolutions#rufusindustrialiot.
Pro Glove accessed on Sep. 5, 2019 from https://www.proglove.com/products/mark2/.

* cited by examiner

*Primary Examiner* — Corey N Skurdal
(74) *Attorney, Agent, or Firm* — Morgan Law Offices, PLC

(57) ABSTRACT

An apparel wearable on a hand of a user is disclosed herein. The apparel includes a wrist brace, a case for supporting a device, and an activation strap for activating the device supported on the case. The wrist brace is wearable on a wrist of the user. The case is configured for housing a device therein, wherein the case can be removable attached to the wrist brace. The activation strap is anchored at a location on the case, wherein the location overlaps with an activation switch of the device, wherein the activation strap activates the activation switch on being pulled by the user. The device can be a barcode scanner, in accordance with one embodiment.

10 Claims, 5 Drawing Sheets

BARCODE SCANNER GLOVE WITH THUMB ACTIVATION

TECHNICAL FIELD

The present disclosure relates generally to a bar code scanner glove that facilitates convenient activation of the device supported thereon.

BACKGROUND

Barcodes and QR codes are machine-readable, optical labels that store information about an item or product and typically provided on the packaging of the product. Barcode scanners (or barcode readers) are devices that optically scan barcodes to decode the data embedded thereon. In general, the barcode scanner illuminates the code and detects reflected light to create an analog signal that is received by a decoder. The signal is interpreted and converted to a character or numeric string. Bar code scanners come in different designs and styles. One of the most common barcode scanners is hand-held device that requires the user to depress a button to activate a single scan. Although these are useful and widely used, continually pressing a button can become tiresome particularly when hundreds of items need to be scanned. Not only can the finger become tired, repetitious movements can cause physical stress and even long-term damage.

SUMMARY

A bar code scanner glove includes an apparel wearable on a hand of a user includes a wrist brace wearable on a wrist of the user. The apparel further includes a case for housing a device therein and configured for removable attachment on the wrist brace. An activation strap is anchored at a location on the case, wherein the location overlaps with an activation switch of the device, wherein the activation strap activates the activation switch on being maneuvered by the user.

DETAILED DESCRIPTION OF EXAMPLE EMBODIMENTS

Example embodiments of the disclosure now will be described more fully hereinafter with reference to the accompanying drawings, in which example embodiments are shown. The concepts discussed herein may, however, be embodied in many different forms and should not be construed as limited to the example embodiments set forth herein; rather, these embodiments are provided so that this disclosure will be thorough and complete, and will fully convey the scope to those of ordinary skill in the art. Like numbers refer to like elements but not necessarily the same or identical elements throughout.

Figure 1:
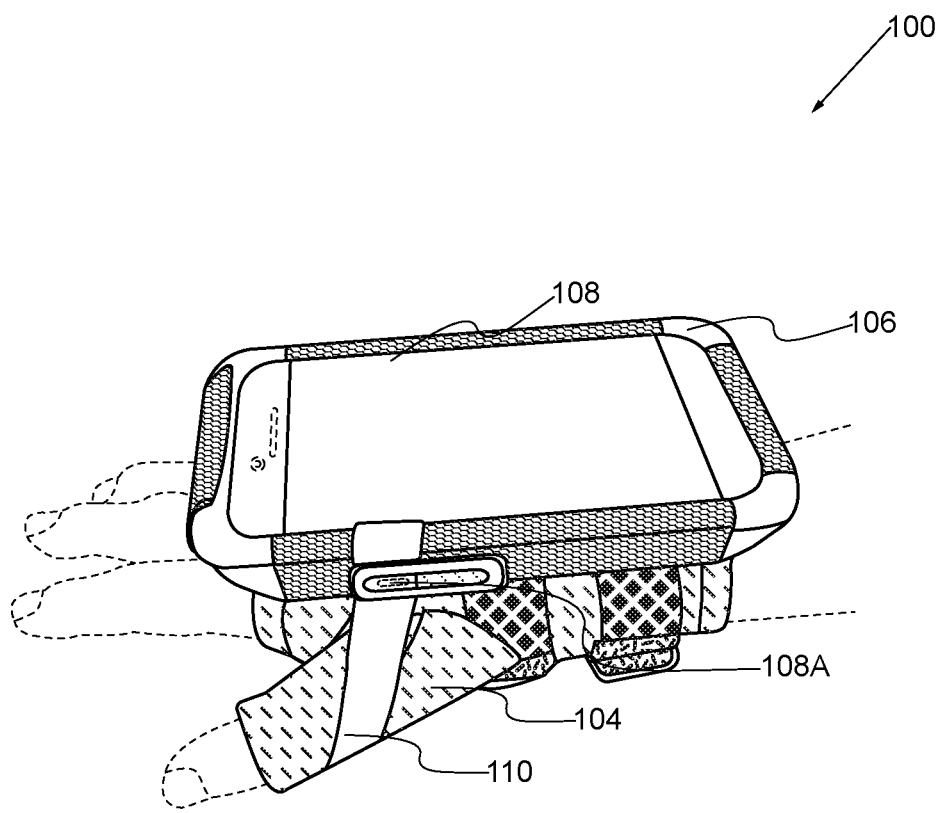
FIG. 1 shows a perspective view of a hand apparel worn by the user for supporting a device thereon, according to a first embodiment of the disclosure.

Referring to FIG. 1, a perspective view of a hand apparel 100 worn by the user for supporting a device 102 thereon, according to a first embodiment of the disclosure, is illustrated. The hand apparel 100 includes a wrist brace 104 and a case 106 removably attachable to the wrist brace 104. In a preferred embodiment, the removable attachment of the case 106 on the wrist brace 104 is facilitated via hook and loop fasteners. The case 106 is configured to house a device therein. In accordance with one embodiment, the device may be a barcode scanner 108. The wrist brace 104 is an apparel of the type similar to a hand glove. The wrist brace 104, as seen in FIG. 1, includes a knuckle accommodating region 104A and a thumb accommodating region 104B. In an alternative embodiment, the wrist brace 104 may have the provision to cover the entire palm and fingers of the user for providing warmth in winter along with the utility of facilitating easy and convenient activation of the barcode scanner 108.

Figure 2:
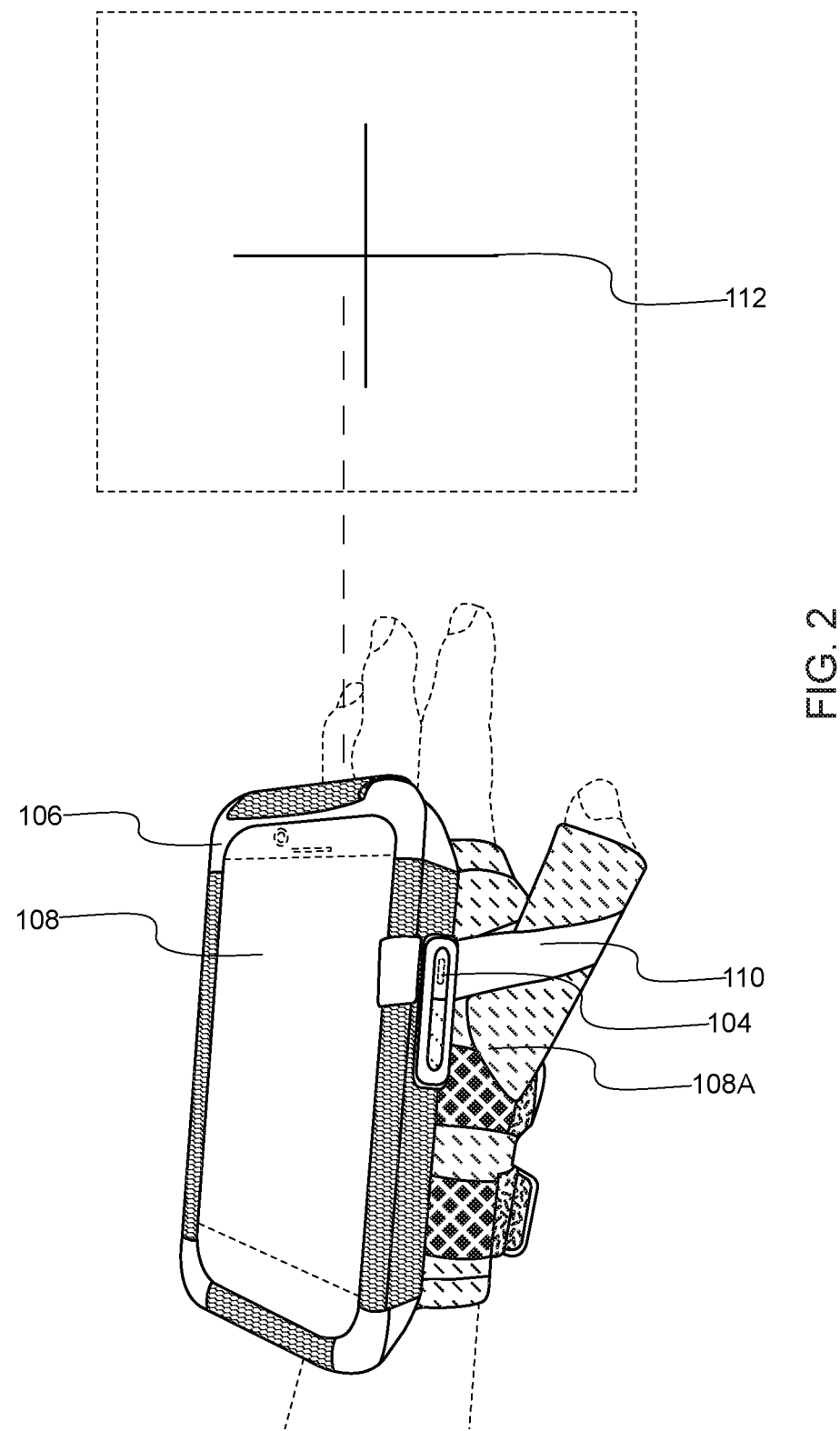
FIG. 2 shows a perspective view of the hand apparel being worn and used for activating the device, according to the first embodiment of the disclosure.

Referring to FIG. 2, a perspective view of the hand apparel being worn and used for activating the device, according to the first embodiment of the disclosure, is illustrated. As seen in FIG. 2, the apparel 100 is configured to securely hold the barcode scanner 108 thereon, while allowing the user to use their thumb for activating the barcode scanner 108. More specifically, the apparel 100 includes an activation strap 110. The activation strap 110 is anchored at a location on the case 106, and a portion below the anchor overlaps with an activation switch 108A of the device (barcode scanner 108) and exits through a aperture, wherein the activation strap 110 activates the activation switch 108A on being pulled by the user. In accordance with an embodiment, the user may insert their thumb within the activation strap to maneuver the activation strap 110. In doing so, the activation strap 110 presses against the activation switch 108A of the barcode scanner 108. More particularly, as the activation strap 110 is pulled downwardly/outwardly by the user's thumb, the strap tightens against the activation switch 108A, pressing s the activation switch causing the barcode scanner to operate. After the scan, the activation strap 110 adjacent the activation switch 108A tends to relax again. The activation of the barcode scanner 108 is indicated by the activation of a light source of the barcode scanner 108, which has been denoted by light projection 112 in FIG. 2. In operation, the light projection 112 may appear on the barcode being scanned by the barcode scanner 108.

Figure 3:
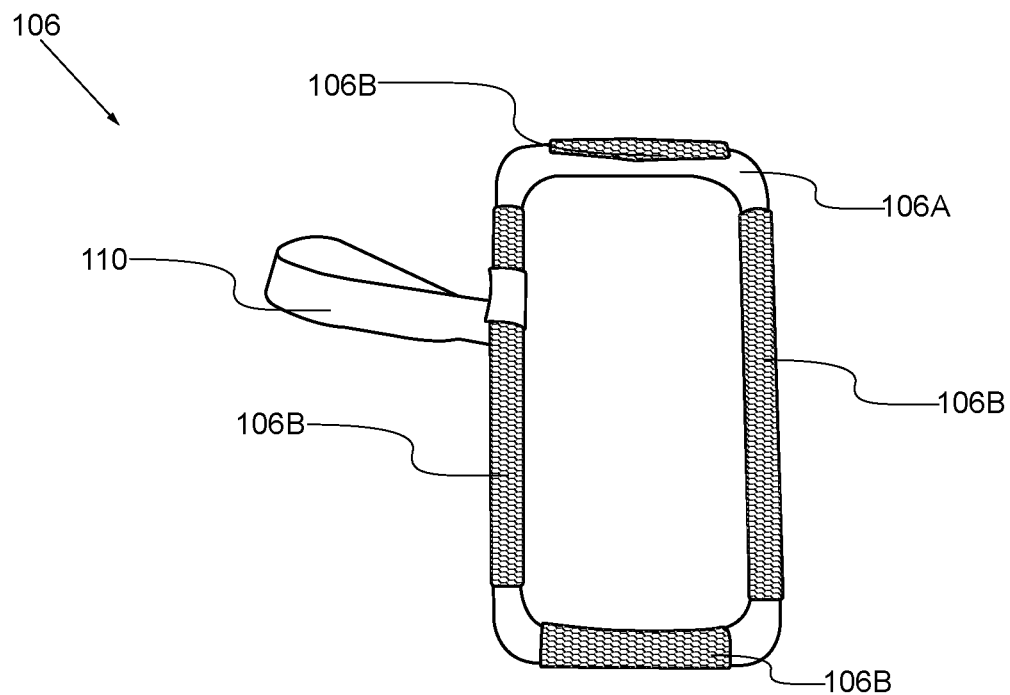
FIG. 3 shows a top view of a case of the apparel used for housing the device therein, according to the first embodiment of the disclosure.

Referring to FIG. 3, a top view of the case 104 of the apparel 100 used for housing the barcode scanner therein, according to the first embodiment of the disclosure, is illustrated. The case 106 includes rigid walls 106A, with cushion cladding 106B configured thereon for protecting the barcode scanner 108 in case of accidental falls.

Figure 4:
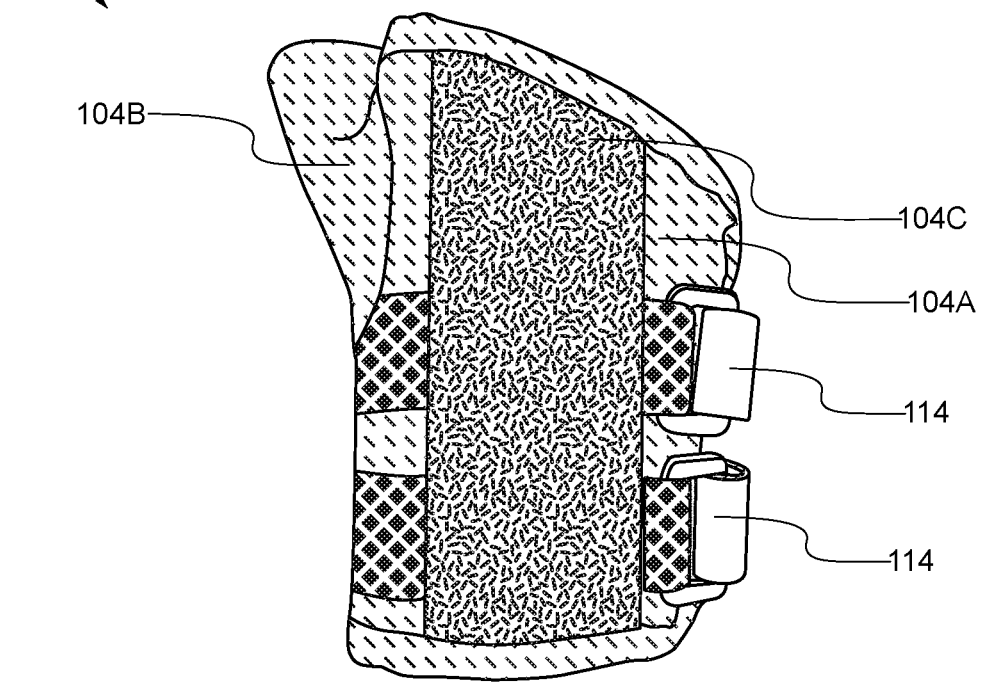
FIG. 4 shows a top view of the wrist brace of the apparel, according to the first embodiment of the disclosure.

Referring to FIG. 4, a top view of the wrist brace of the apparel, according to the first embodiment of the disclosure, is illustrated. The wrist brace 104 includes the knuckle accommodating region 104A and the thumb accommodating region 104B. An advantageous aspect of the thumb accommodating region 104B is that it keeps the wrist brace 104 from sliding side-to-side when rotated. More specifically, as user maneuvers the activation strap 110 using the thumb, it may cause the wrist brace 104 to rotate but the presence of the thumb accommodating region 104B prevents such rotations. The wrist brace 104 further includes a securement strap 104C. In an embodiment, the securement strap 104C may be a hook and loop strap. The securement strap 104C is configured on the wrist brace 104 for facilitating the attachment of the case 106 thereon. The bottom of the case 106 may also be provided with a complementary hook and loop strap for attaching to the securement strap 104C. The wrist brace 104 may be made of any fabric. The wrist brace 104 may further include at least one fitment strap 114. The fitment strap 114 may be configured adjacent a distal end of the wrist brace 104 for facilitating secure fitment of the wrist brace 104 on the forearm of the user. In an embodiment, the fitment strap 114 may be a hook and loop strap.

Figure 5:
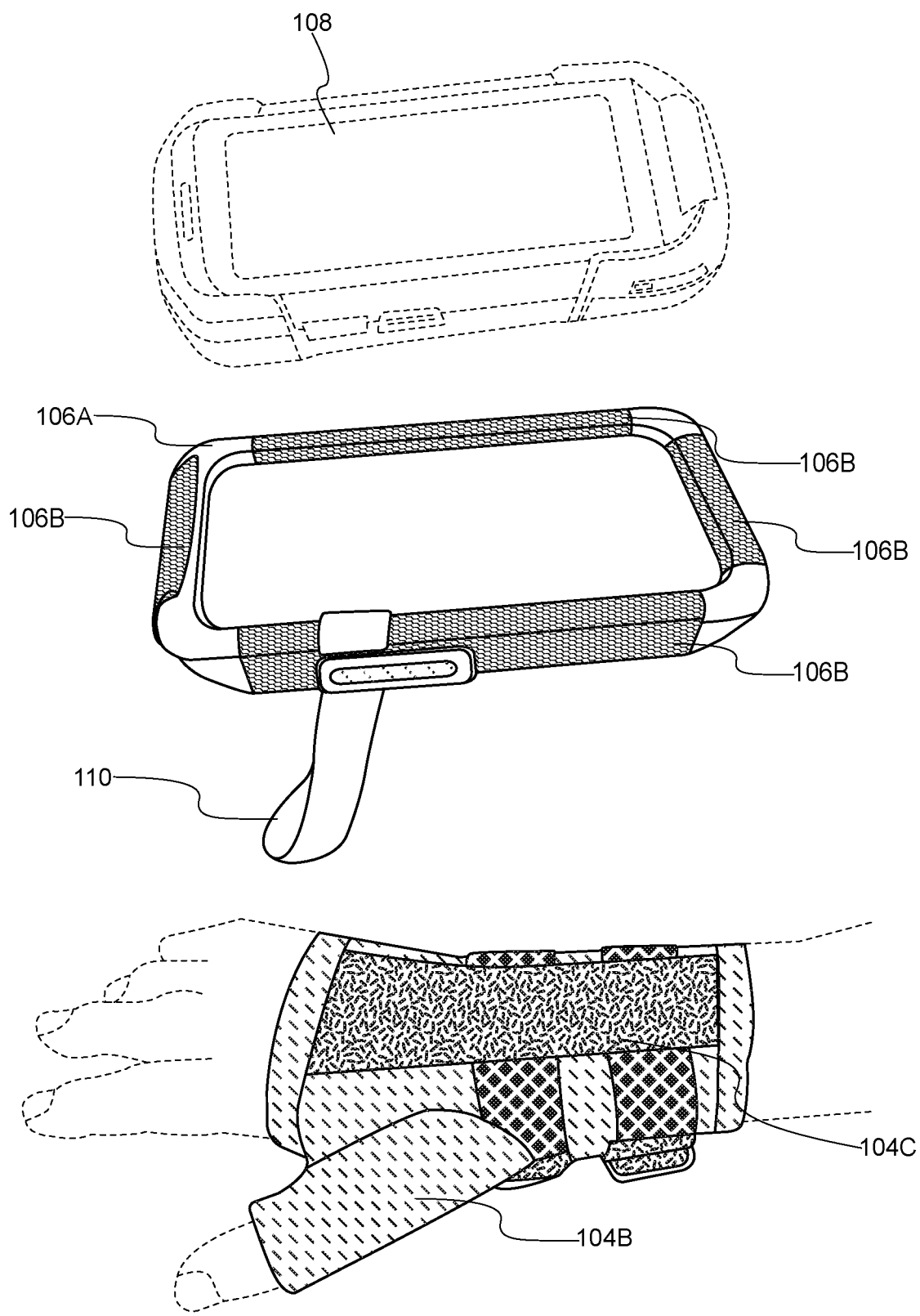
FIG. 5 shows an exploded perspective view of the different elements of the apparel, according to the first embodiment of the disclosure.

Referring to FIG. 5, an exploded perspective view of the different elements of the apparel 100, according to the first embodiment of the disclosure, is illustrated. The barcode scanner 108 is accommodated within the case 106. The case 106, in turn, may be attached to the wrist brace 104. The removable attachment of the case 106 to the wrist brace 104 is facilitated via securement straps provided on the wrist brace 104 as well as on the bottom of the case 106, wherein the securement straps may be hook and loop straps.

Figure 6:
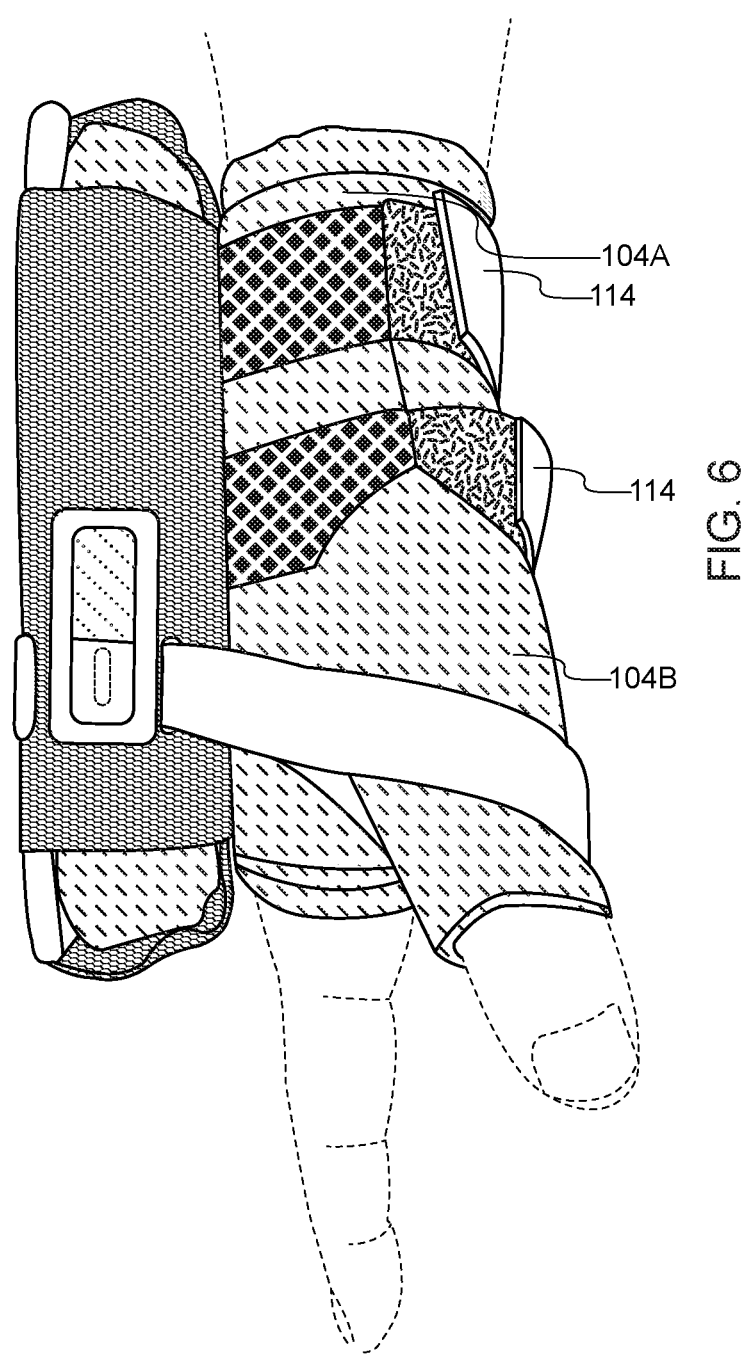
FIG. 6 shows a side view of the apparel, according to the first embodiment of the disclosure.

Referring to FIG. 6, a side view of the apparel, according to the first embodiment of the disclosure, is illustrated. The attachment of the securement straps provided on the bottom of the case 106 and on the wrist brace 104 is clearly seen in FIG. 6.

In operation, a method for activating a switch 108A of a barcode scanner 108 includes wearing, on a user's arm, a wrist brace 104 of an apparel 100 for supporting the barcode scanner 108 thereon; placing the barcode scanner 108 in a case 106 of the apparel 100; removably attaching the case 106 containing the barcode scanner 108 to the wrist brace 104; inserting the thumb of the user in an activation strap 110 of the apparel 110, wherein the activation strap 110 is anchored at a location on the case 106, wherein the location overlaps with the switch 108A of the barcode scanner 108; and maneuvering the thumb of the user subsequent to being inserted within the activation strap for facilitating application of a pressing force on the switch of the barcode scanner.

Although the features, functions, components, and parts have been described herein in accordance with the teachings of the present disclosure, the scope of coverage of this patent is not limited thereto. On the contrary, this patent covers all embodiments of the teachings of the disclosure that fairly fall within the scope of permissible equivalents.

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims. Although specific terms are employed herein, they are used in a generic and descriptive sense only and not for purposes of limitation.

What is claimed is:

1. An apparel wearable on a hand of a user, the apparel comprising:
   a wrist brace wearable on a wrist of the user;
   a case for housing a device therein, the case configured for removable attachment on the wrist brace; and
   an activation strap anchored at a location on the case, wherein the location overlaps with an activation switch of the device, wherein the activation strap activates the activation switch on being maneuvered by the user.

2. The apparel according to claim 1, wherein the activation strap is looped and hangs from the case.

3. The apparel according to claim 2, wherein the removable attachment of the case on the wrist brace is facilitated by hook and loop straps.

4. The apparel according to claim 2, wherein the wrist brace has a knuckle accommodating region and a thumb accommodating region.

5. The apparel according to claim 1, further comprising at least one fitment strap configured on the wrist brace.

6. The apparel according to claim 5, wherein the at least one fitment strap includes hook and loop straps.

7. The apparel according to claim 1, wherein the device is a barcode scanner.

8. The apparel according to claim 7, wherein the pulling of the activation strap facilitates application of a pressing force on the activation switch of the barcode scanner.

9. The apparel according to claim 8, wherein the pulling of the activation strap is facilitated by maneuvering of the thumb of the user subsequent to being inserted within the activation strap.

10. A method for activating a switch of a barcode scanner, the method comprising:
    wearing, on a user's arm, a wrist brace of an apparel for supporting the barcode scanner thereon;
    placing the barcode scanner in a case of the apparel;
    removably attaching the case containing the barcode scanner to the wrist brace;
    inserting the thumb of the user in an activation strap of the apparel, wherein the activation strap is anchored at a location on the case, wherein the location overlaps with the switch of the barcode scanner; and
    maneuvering the thumb of the user subsequent to being inserted within the activation strap for facilitating application of a pressing force on the switch of the barcode scanner.

* * * * *